(12) United States Patent
Melsheimer

(10) Patent No.: US 8,137,291 B2
(45) Date of Patent: Mar. 20, 2012

(54) WIRE GUIDE HAVING DISTAL COUPLING TIP

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1190 days.

(21) Appl. No.: 11/549,466

(22) Filed: Oct. 13, 2006

(65) Prior Publication Data

US 2007/0118052 A1     May 24, 2007

Related U.S. Application Data

(60) Provisional application No. 60/730,776, filed on Oct. 27, 2005.

(51) Int. Cl.
A61M 25/00 (2006.01)
(52) U.S. Cl. .......................................... 600/585
(58) Field of Classification Search ........... 600/433, 600/434, 585; 604/164.13
See application file for complete search history.

(56) References Cited

U.S. PATENT DOCUMENTS

| | | | |
|---|---|---|---|
| 892,472 A * | 7/1908 | Walker | 606/106 |
| 2,657,691 A | 11/1953 | Nordstrom, Jr. | |
| 3,521,620 A | 7/1970 | Cook | |
| 3,547,103 A | 12/1970 | William | |
| 3,656,680 A | 4/1972 | Nomura | |
| 3,739,784 A | 6/1973 | Itoh | |
| 3,890,977 A | 6/1975 | Wilson | |
| 4,548,206 A | 10/1985 | Osborne | |
| 4,569,347 A | 2/1986 | Frisbie | |
| 4,601,713 A | 7/1986 | Fuqua | |
| 4,650,472 A | 3/1987 | Bates | |
| 4,665,906 A | 5/1987 | Jervis | |
| 4,824,435 A | 4/1989 | Giesy et al. | |
| 4,921,483 A | 5/1990 | Wijay et al. | |
| 4,925,445 A | 5/1990 | Sakamoto et al. | |
| 4,934,380 A | 6/1990 | De Toledo | |
| 4,984,581 A | 1/1991 | Stice | |
| 5,003,990 A | 4/1991 | Osypka | |
| 5,046,497 A | 9/1991 | Millar | |
| 5,069,226 A | 12/1991 | Yamauchi et al. | |
| 5,105,818 A | 4/1992 | Christian et al. | |
| 5,129,890 A | 7/1992 | Bates et al. | |
| 5,131,407 A | 7/1992 | Ischinger et al. | |
| 5,159,861 A | 11/1992 | Anderson | |

(Continued)

FOREIGN PATENT DOCUMENTS

EP     0 436 303 A1     10/1991

(Continued)

OTHER PUBLICATIONS

International Search Report—PCT/US2006/040843 (Jan. 31, 2007).

(Continued)

*Primary Examiner* — Max Hindenburg
*Assistant Examiner* — Jonathan M Foreman
(74) *Attorney, Agent, or Firm* — Brinks Hofer Gilson & Lione

(57) ABSTRACT

A coupling wire guide generally includes a main body defined by a first wire wound around a safety wire. A first loop is defined by an enlarged revolution of the first wire within a distal portion of the main body. The first loop is sized to receive a previously introduced wire guide for coupling the two wire guides.

17 Claims, 1 Drawing Sheet

U.S. PATENT DOCUMENTS

| | | | |
|---|---|---|---|
| 5,213,111 | A | 5/1993 | Cook et al. |
| 5,234,003 | A | 8/1993 | Hall |
| 5,242,759 | A | 9/1993 | Hall |
| 5,243,996 | A | 9/1993 | Hall |
| 5,251,640 | A | 10/1993 | Osborne |
| 5,257,974 | A * | 11/1993 | Cox .................. 604/103.05 |
| 5,267,958 | A | 12/1993 | Buchbinder et al. |
| 5,306,261 | A | 4/1994 | Alliger et al. |
| 5,318,527 | A | 6/1994 | Hyde et al. |
| 5,325,746 | A | 7/1994 | Anderson |
| 5,328,472 | A | 7/1994 | Steinke et al. |
| 5,328,480 | A | 7/1994 | Milker et al. |
| 5,344,413 | A | 9/1994 | Allman et al. |
| 5,354,257 | A | 10/1994 | Roubin et al. |
| 5,383,853 | A | 1/1995 | Jung et al. |
| 5,402,799 | A | 4/1995 | Colon et al. |
| 5,449,362 | A | 9/1995 | Chaisson et al. |
| 5,456,680 | A | 10/1995 | Taylor et al. |
| 5,488,959 | A | 2/1996 | Ales |
| 5,527,326 | A * | 6/1996 | Hermann et al. ............ 606/159 |
| 5,597,378 | A | 1/1997 | Jervis |
| 5,667,521 | A | 9/1997 | Keown |
| 5,738,667 | A | 4/1998 | Solar |
| 5,762,070 | A | 6/1998 | Nagamatsu |
| 5,776,079 | A | 7/1998 | Cope et al. |
| 5,776,100 | A | 7/1998 | Forman |
| 5,797,857 | A | 8/1998 | Obitsu |
| 5,810,876 | A | 9/1998 | Kelleher |
| 5,827,225 | A | 10/1998 | Ma Schwab |
| 5,873,842 | A | 2/1999 | Brennen et al. |
| 5,882,333 | A | 3/1999 | Schaer et al. |
| 5,891,056 | A | 4/1999 | Ramzipoor |
| 5,893,868 | A | 4/1999 | Hanson et al. |
| 5,993,424 | A | 11/1999 | Lorenzo et al. |
| 5,997,526 | A | 12/1999 | Giba et al. |
| 6,007,517 | A | 12/1999 | Anderson |
| 6,139,510 | A | 10/2000 | Palermo |
| 6,217,567 | B1 | 4/2001 | Zadno-Azizi et al. |
| 6,221,066 | B1 | 4/2001 | Ferrera et al. |
| 6,248,092 | B1 | 6/2001 | Miraki et al. |
| 6,254,549 | B1 | 7/2001 | Ramzipoor |
| 6,254,550 | B1 | 7/2001 | McNamara et al. |
| 6,290,693 | B1 | 9/2001 | Jung, Jr. et al. |
| 6,299,612 | B1 * | 10/2001 | Ouchi .............................. 606/47 |
| 6,306,141 | B1 | 10/2001 | Jervis |
| 6,309,404 | B1 | 10/2001 | Krzyzanowski |
| 6,348,041 | B1 | 2/2002 | Klint |
| 6,348,045 | B1 | 2/2002 | Malonek et al. |
| 6,348,056 | B1 * | 2/2002 | Bates et al. ................... 606/114 |
| 6,383,146 | B1 | 5/2002 | Klint |
| 6,471,697 | B1 | 10/2002 | Lesh |
| 6,475,167 | B1 | 11/2002 | Fleming et al. |
| 6,500,130 | B2 | 12/2002 | Kinsella et al. |
| 6,502,606 | B2 | 1/2003 | Klint |
| 6,517,518 | B2 | 2/2003 | Nash et al. |
| 6,530,899 | B1 | 3/2003 | Savage |
| 6,569,151 | B1 | 5/2003 | Nash et al. |
| 6,596,963 | B2 | 7/2003 | Kelly |
| 6,605,049 | B1 | 8/2003 | Wagner et al. |
| 6,613,002 | B1 | 9/2003 | Clark et al. |
| 6,638,372 | B1 | 10/2003 | Abrams et al. |
| 6,682,608 | B2 | 1/2004 | Abrams et al. |
| 6,687,548 | B2 * | 2/2004 | Goode .......................... 607/119 |
| 6,805,676 | B2 | 10/2004 | Klint |
| 6,872,192 | B2 | 3/2005 | Nash et al. |
| 7,074,197 | B2 | 7/2006 | Reynolds et al. |
| 7,076,285 | B2 | 7/2006 | Windheuser et al. |
| 7,229,431 | B2 | 6/2007 | Houser et al. |
| 7,527,606 | B2 | 5/2009 | Oepen |
| 2002/0058888 | A1 | 5/2002 | Biagtan et al. |
| 2002/0169457 | A1 | 11/2002 | Quinn |
| 2002/0183763 | A1 | 12/2002 | Callol et al. |
| 2003/0028127 | A1 | 2/2003 | Balzum et al. |
| 2003/0120208 | A1 | 6/2003 | Houser et al. |
| 2003/0139750 | A1* | 7/2003 | Shinozuka et al. ............ 606/113 |
| 2004/0073108 | A1 | 4/2004 | Saeed et al. |
| 2004/0116957 | A1 | 6/2004 | Nishide |
| 2004/0199087 | A1 | 10/2004 | Swain et al. |
| 2004/0215208 | A1 | 10/2004 | Foushee et al. |
| 2005/0027212 | A1 | 2/2005 | Segner et al. |
| 2005/0075647 | A1 | 4/2005 | Walters et al. |
| 2005/0143770 | A1 | 6/2005 | Carter et al. |
| 2005/0148902 | A1 | 7/2005 | Minar et al. |
| 2005/0197663 | A1 | 9/2005 | Soma et al. |
| 2005/0209533 | A1 | 9/2005 | Lorenz |
| 2005/0267442 | A1 | 12/2005 | Von Oepen |
| 2005/0283122 | A1 | 12/2005 | Nordgren |
| 2006/0020256 | A1 | 1/2006 | Bell et al. |
| 2006/0100544 | A1 | 5/2006 | Ayala et al. |
| 2006/0100545 | A1 | 5/2006 | Ayala et al. |
| 2007/0060908 | A1 | 3/2007 | Webster et al. |
| 2007/0149946 | A1 | 6/2007 | Viswanathan et al. |
| 2007/0167065 | A1 | 7/2007 | Melsheimer et al. |
| 2007/0185414 | A1 | 8/2007 | Urbanski et al. |
| 2007/0191790 | A1 | 8/2007 | Eells et al. |

FOREIGN PATENT DOCUMENTS

| | | |
|---|---|---|
| EP | 0829269 A1 | 3/1998 |
| EP | 1057500 A1 | 12/2000 |
| EP | 1 428 546 A2 | 6/2004 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 01/03764 A1 | 1/2001 |
| WO | WO 02/094364 A2 | 11/2002 |
| WO | WO2004/033016 | 4/2004 |
| WO | WO 2004/049970 A2 | 6/2004 |
| WO | WO 2004/050161 A1 | 6/2004 |
| WO | WO 2005/011530 A1 | 2/2005 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A1 | 8/2007 |
| WO | WO 2007/089893 A1 | 8/2007 |

OTHER PUBLICATIONS

International Search Report—PCT/US2007/002743 (Jun. 14, 2007).
International Search Report—PCT/US2007/002741 (Jul. 9, 2007).
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 16, 2008 U.S. Appl. No. 11/763,355 issued in related application.
Office Action dated May 30, 2008 U.S. Appl. No. 11/507,805 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).
Office Action dated Nov. 15, 2007 issued in related U.S. Appl. No. 11/652,430.
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 20, 2008 U.S. Appl. No. 11/763,355 issued in co-pending application.
Office Action dated Nov. 21, 2008 U.S. Appl. No. 11/549,473 issued in co-pending application.
Office Action dated Nov. 21, 2008 U.S. Appl. No. 11/699,171 issued in co-pending application.
Office Action dated Nov. 11, 2008 U.S. Appl. No. 11/652,430 issued in co-pending application.
Advisory Action dated Jan. 16, 2009 U.S. Appl. No. 11/507,805 issued in co-pending application.
International Preliminary Report on Patentability and Written Opinion (Jul. 24, 2008) PCT/US2007/001066.

Office Action dated Sep. 26, 2008 U.S. Appl. No. 11/706,548 issued in related application.
Office Action dated Oct. 7, 2008 U.S. Appl. No. 11/507,993 issued in related application.
Office Action dated Oct. 15, 2008 U.S. Appl. No. 11/699,174 issued in related application.
International Search Report & Written Opinion (Jan. 3, 2008).
Notification of Transmittal of International Preliminary Report on Patentability (Jan. 10, 2008).
Office Action dated Jun. 4, 2009 U.S. Appl. No. 11/549,473 issued in co-pending application.
Office Action dated Jun. 9, 2009 U.S. Appl. No. 11/763,355 issued in co-pending application.
Office Action dated Jun. 12, 2009 U.S. Appl. No. 11/699,174 issued in co-pending application.
Advisory Action dated Jun. 25, 2009 U.S. Appl. No. 11/549,481 issued in co-pending application.
Advisory Action dated Jun. 22, 2009 U.S. Appl. No. 11/706,548 issued in co-pending application.
Office Action dated Jun. 23, 2009 U.S. Appl. No. 11/652,430 issued in co-pending application.
Office Action dated Aug. 3, 2009 U.S. Appl. No. 11/699,174 issued in co-pending application.
Office Action dated Sep. 16, 2009 U.S. Appl. No. 11/549,481 issued in co-pending application.
Office Action dated Oct. 1, 2009 U.S. Appl. No. 11/763,355 issued in co-pending application.
Office Action dated Oct. 14, 2009 U.S. Appl. No. 11/507,805 issued in co-pending application.
Office Action dated Oct. 23, 2009 U.S. Appl. No. 11/706,548 issued in co-pending application.
Office Action dated Dec. 9, 2009 U.S. Appl. No. 11/652,430 issued in co-pending application.
Office Action dated Dec. 14, 2009 U.S. Appl. No. 11/507,993 issued in co-pending application.
Office Action dated Jan. 19, 2010 U.S. Appl. No. 11/699,171 issued in co-pending application.
Office Action dated Apr. 2, 2010 U.S. Appl. No. 11/507,805 issued in co-pending application.
Office Action dated Apr. 6, 2010 U.S. Appl. No. 11/763,355 issued in co-pending application.
Office Action dated Mar. 12, 2010 U.S. Appl. No. 11/699,174 issued in co-pending application.
Office Action dated Apr. 21, 2010 U.S. Appl. No. 11/706,548 issued in co-pending application.
Advisory Action dated Mar. 6, 2009 U.S. Appl. No. 11/652,430 issued in co-pending application.
Office Action dated Mar. 30, 2009 U.S. Appl. No. 11/699,174 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 8, 2009 U.S. Appl. No. 11/699,171 issued in co-pending application.
Office Action dated May 14, 2009 U.S. Appl. No. 11/507,993 issued in coo-pending application.
Office Action Restriction dated Mar. 3, 2008 U.S. Appl. No. 11/507,805 issued in related application.
Office Action Restriction dated Jul. 2, 2008 U.S. Appl. No. 11/699,171 issued in related application.
International Search Report/Written Opinion—PCT/US2006/040843 (Feb. 7, 2007).
International Preliminary Report on Patentability—PCT/US2007/002741 (Jun. 25, 2008).
International Search Report—PCT/US2006/042184 (Mar. 1, 2007).
International Search Report—PCT/US2007/001066 (Jun. 18, 2007).
International Search Report—PCT/US2007/004827 (Oct. 26, 2007).
The Journal of Invasive Cardiology entitled "Use of a Second Buddy Wire During Percutaneous Coronary Interventions: A Simple Solution for Some Challenging Situations" dated Apr. 25, 2005, pp. 1-8.
Notice of Allowance dated Jan. 25, 2010 U.S. Appl. No. 11/549,473 issued in co-pending application.
Notice of Allowance dated Mar. 25, 2010 U.S. Appl. No. 11/549,481 issued in co-pending application.
Notice of Allowance dated May 19, 2010 U.S. Appl. No. 11/699,174 issued in co-pending application.
Notice of Allowance dated May 27, 2010 U.S. Appl. No. 11/699,171 issued in co-pending application.
Notice of Allowance dated Jun. 3, 2010 U.S. Appl. No. 11/652,430 issued in co-pending application.
Office Action (Final) dated Jun. 17, 2010 U.S. Appl. No. 11/507,993 issued in co-pending application.
Advisory Action dated Jun. 17, 2010 U.S. Appl. No. 11/507,805 issued in co-pending application.
Advisory Action dated Jun. 24, 2010 U.S. Appl. No. 11/763,355 issued in co-pending application.
Advisory Action dated Jun. 28, 2010 U.S. Appl. No. 11/706,548 issued in co-pending application.
Office Action dated Dec. 8, 2010 U.S. Appl. No. 11/507,993 issued in co-pending application.
Office Action dated Dec. 28, 2010 U.S. Appl. No. 11/507,805 issued in co-pending application.

* cited by examiner

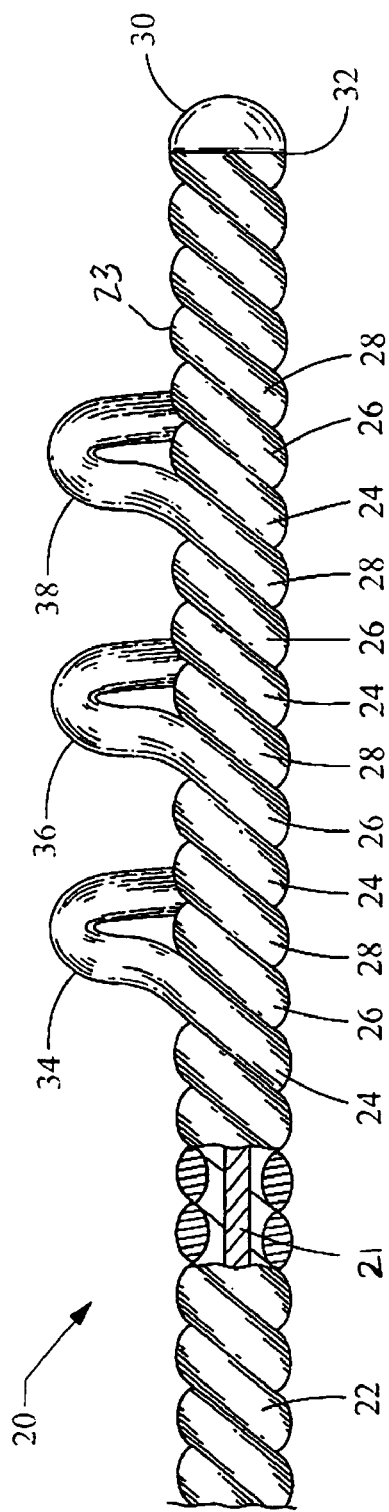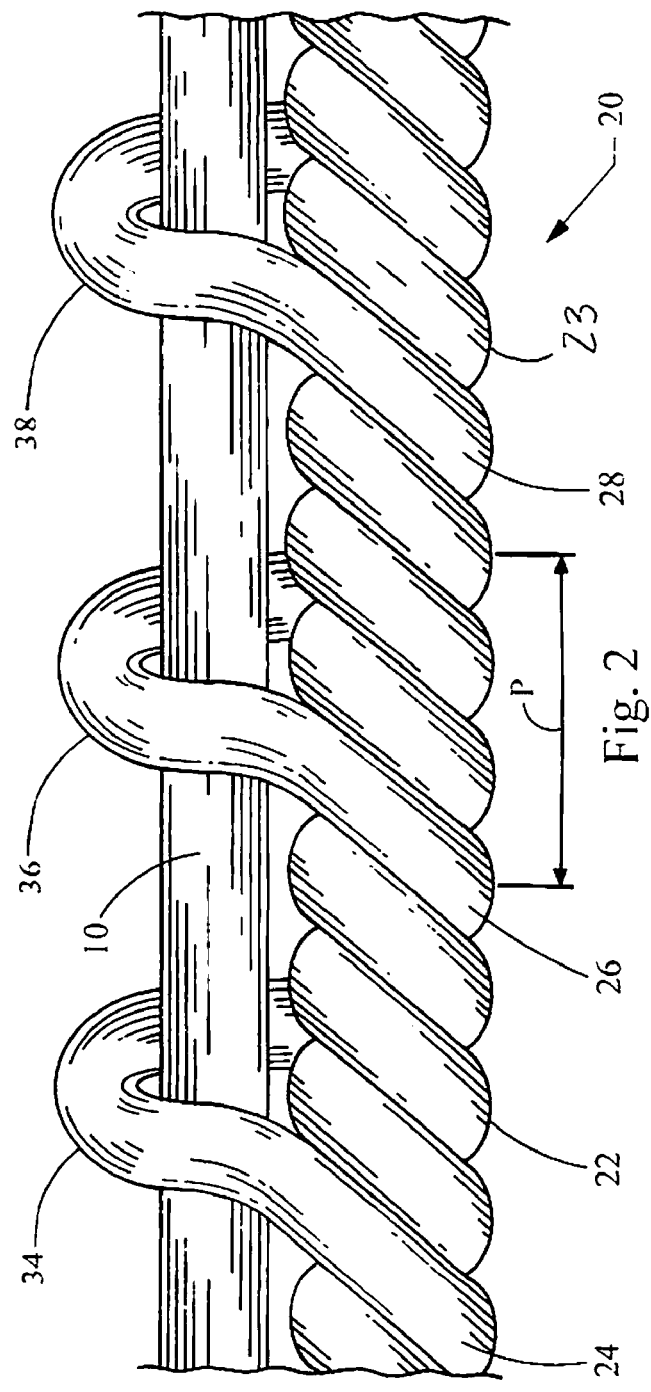

WIRE GUIDE HAVING DISTAL COUPLING TIP

CROSS-REFERENCE TO RELATED APPLICATIONS

This application claims the benefit of U.S. Provisional Application Ser. No. 60/730,776 filed on Oct. 27, 2005, entitled "WIRE GUIDE HAVING DISTAL COUPLING TIP", the entire contents of which are incorporated herein by reference.

FIELD OF THE INVENTION

This invention relates generally to a wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for percutaneous interventional procedures that may be easily and reliably traversed through the vasculature to a position proximate a previously introduced wire guide.

BRIEF SUMMARY OF THE INVENTION

The present invention provides a supporting wire guide for intracorporeal procedures that may be easily and reliably traversed through the vasculature to a position proximate a previously introduced wire guide. The supporting wire guide is a coupling wire guide that is structured to be slidably coupled to the previously introduced wire guide. In one embodiment constructed in accordance with the teachings of the present invention, the coupling wire guide generally includes a main body defined by a first wire and a second wire wound around a safety wire. A first loop is defined by an enlarged revolution of the first wire within a distal portion of the main body. A second loop is defined by an enlarged revolution of the second wire within the distal portion of the main body. The first and second loops are sized to receive the previously introduced wire guide for coupling of the two wire guides.

According to more detailed aspects of this embodiment of the present invention, the first and second loops are axially spaced apart. Generally, the first and second loops are spaced apart a distance about equal to the pitch of the coiled first and second wires. The coupling wire guide may further include a third wire wound around the safety wire, wherein the first, second and third wires define the main body. Here, a third loop is also provided, and is defined by an enlarged revolution of the third wire within the distal portion of the main body. The first, second and third loops are axially spaced apart, preferably a distance about equal to the pitch of the coiled first, second and third wires.

A method of forming the coupling wire guide is also provided in accordance with the teachings of the present invention. The method generally comprising the steps of selecting a wire guide formed of a first wire twisted to define a main body portion, backtwisting a portion of the main body, forming an enlarged revolution of the first wire to thereby define a first loop, and twisting the main body to reform the wire guide having the first loop. In this manner, the coupling wire guide may again be backtwisted and twisted to remove the first loop, and thus these steps may be repeated multiple times for multiple formation or removal of the first loop. Similarly, the axial location of the first loop may be shifted by manipulating the respective wire. Multiple filar wire guides are preferably employed whereby multiple loops are formed. Accordingly, the coupling wire guide may be returned to its normal configuration having a standard profile, and the formation and position of the loops may be selectively provided according to the needs of the medical professional and patient.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a side view, partially cut-away, of a coupling wire guide constructed in accordance with the teachings of the present invention; and FIG. 2 is an enlarged side view, partially cut-away, showing the coupling wire guide of FIG. 1 coupled to a previously introduced wire guide.

DETAILED DESCRIPTION OF THE INVENTION

Turning now to the figures, FIGS. 1 and 2 depict a coupling wire guide 20 constructed in accordance with the teachings of the present invention. The coupling wire guide 20 includes a main body 22 having a distal portion 23. The main body 22, including the distal portion 23, is defined by a first wire 24, a second wire 26, and a third wire 28. The first, second and third wires 24, 26, 28 are disposed over a safety wire 21, which in turn is connected to an end cap 30 defining a distal tip 32 of the coupling wire guide 20. Particularly, the first, second and third wires 24, 26, 28 are wound around the safety wire 21, preferably by coiling the wires in parallel to form three phases or filars. It can be seen in the figures that the wires 24, 26, 28 are immediately adjacent each other in the wind.

The coupling wire guide 20 is structured for coupling to a previously introduced wire guide 10, depicted as a solid wire in FIG. 2. While wire guides are often used in percutaneous interventional procedures, it will be recognized by those skilled in the art that the wire guides of the present invention may also be employed in endoscopic or other intracorporeal procedures. It will also be recognized that the previously introduced wire guide 10, as well as the main body 22 of the coupling wire guide 20, may take numerous forms as many types of wire guides are known in the art, including a solid wire, a tubular wire, a coiled wire and combinations thereof. For example, the previously introduced wire guide 10 may simply comprise a mandrel alone, or a combination of mandrel and coiled wire, as is shown in U.S. Pat. No. 5,243,996, the disclosure of which is incorporated herein by reference in its entirety. With regard to the coupling wire guide 20, at least the distal portion 23 preferably has a multiple filar construction, such as the coiled first, second and third wires 24, 26, 28 described above, although a single coiled wire may still employ the teachings of the present invention.

In order to provide the coupling function, the coupling wire guide 20 includes a first loop 34, a second loop 36, and a third loop 38. As best seen in FIG. 2, the loops 34, 36, 38 are each sized to receive a previously introduced wire guide 10 therein. Each loop 34, 36, 38 is formed in a similar manner, namely by way of an enlarged revolution of the respective first, second or third wire 24, 26, 28. That is, for each revolution of one of the wires 24, 26, 28, the wire spans an axial distance P, also referred to herein as the pitch. The loops 34, 36, 38 are axially spaced from one another such that the wind is progressed to maintain this pitch (i.e. the non-looping wires progress normally) in between each of the loops. Thus, the friction between the wires 24, 26, 28 assists in maintaining the position of the loops 34, 36, 38. For example, in the area of first loop 34 the normal winding position of the second and third wires 26, 28 are maintained while the first wire 24 makes an enlarged revolution to define the first loop 34. Then, once the first wire 24 has returned to its normal position within the wind progression, the second wire 26 then makes its enlarged revolution to define the second loop 36, while the first and third wires 24, 28 continue on their normal progression. As such, once all of the loops 34, 36, 38 have been formed, the first, second and third wires 24, 26, 28 may continue on their normal winding progression to define the remainder of the main body 22.

The wire guides 10, 20 are coupled by placing a proximal end of the previously introduced wire guide 10 through each of the loops 34, 36, 38. The coupling wire guide 20 is then traversed through the vasculature in a normal manner, preferably while holding the previously introduced wire guide 10 in place. To decouple the wire guides 10, 20, the wire guides 10, 20 are moved relative to one another such that a distal end of the previously introduced wire guide 10 passes proximally through and out of each of the loops 34, 36, 38.

It will be recognized that many variations may be employed by the coupling wire guide 20 of the present invention. For example, the main body 22 or at least its distal portion 23 may comprise a winding of only one or two wires, or may comprise a winding of more than three wires. It will also be recognized that a loop does not need to be formed in each of the wires. For example, distal portion 23 may comprise a winding of three wires with single or multiple loops formed in only one or two of the wires. Further, while one set of loops 34, 36, 38 have been depicted, it will be recognized that additional sets of loops may be readily formed. In sum, a wire guide having a single coiled wire may include one or more loops, a wire guide having two or more wires may include one or more loops in one or more of the wires.

By employing multiple loops 34, 36, 38 in the coupling wire guide 20, the medical professional is provided with flexibility in the manner of coupling two wire guides 10, 20. For example, less than all of the loops 34, 36, 38 may be used to couple the wire guides 10, 20, resulting in different levels of coupling support. Additional flexibility is provided since the loops 34, 36, 38 may be formed at any axial position along the length of the coupling wire guide 20, although it is preferred that the loops are formed in a distal portion 23 of the wire guide 20 and adjacent the distal tip 32 thereof, thereby facilitating decoupling of the two wire guides 10, 20 inside the vasculature with minimal relative translation of the two wire guides 10, 20. Further, the size of the loops 34, 36, 38 may be of any area or diameter, and preferably are sized such that the loops may receive numerous sizes of previously introduced wire guides 10 having a range of sizes (diameters).

The wires 24, 26, 28 are preferably formed of a metal or alloy such as stainless steel or Nitinol (Ni—Ti) although any known or future developed wire guide materials may be used, and thus the loops 34, 36, 38 are flexible and may bend or fold to a position close to the wire guide 20. In this manner the distal portion 23 is provided with an extremely low profile that is not significantly greater in size than a standard wire guide. An even lower profile, and specifically a normal configuration of the wire guide 20, may also be achieved through a particular construction of the wire guide 20. That is, the loops 34, 36, 38 may be selectively "removed" from the wire guide 20 through simple manipulation of the wire guide 20, as will be described below.

One method of forming the coupling wire guide 20 described above, as well as removing the loops 34, 36, 38, is through the manipulation of a standard multi-filar wire guide. Taking the three filar wire guide as an example, the twisted wire portion of the wire guide may be clamped at a clamping point proximal to the distal end of the wire guide, such as by pinching the wire guide with one's fingers. The clamping point may include the proximal end of the wire guide. Then, the wire guide is backtwisted (i.e. a portion distal to the clamping point is rotated counter to the winding direction) to loosen the winding of the wires 24, 26, 28. Each of the wires 24, 26, 28 are then grasped and pulled to form an enlarged revolution, i.e. a loop 34, 36, 38. Preferably these loops 34, 36, 38 are positioned and spaced in the manner described above. The portion of the wire guide 20 distal to the loops 34, 36, 38 are twisted again in their normal manner to re-form the wire guide 20.

It will be recognized by those skilled in the art that the method of forming the wire guide 20 described in the preceding paragraph may be reversed once the loops 34, 36, 38 have been formed, whereby the loops 34, 36, 38 may be removed through backtwisting and then proper re-twisting of the wires 24, 26, 28. It will also be recognized that this process may be repeated indefinitely to form more loops, to remove loops, or to shift the position of loops. In fact, the location of the loops 34, 36, 38 may be shifted with little to no backtwisting through simple manipulation of the wires 24, 26, 28 in the area of the loops 34, 36, 38. It will also be recognized by those skilled in the art that other methods may be used to form coupling wire guides in accordance with the teachings of the present invention, such as originally twisting or otherwise initially forming the wire guide with the loops 34, 36, 38. Likewise, it may be desirable in some applications to fix the position of the loops 34, 36, 38, which may be readily accomplished through soldering, welding or other bonding techniques.

Accordingly, it will be recognized by those skilled in the art that the coupling wire guide, by way of formed loops 34, 36, 38, provides a simple and reliable connection to a previously introduced wire guide 10. The loops 34, 36, 38 provide an extremely secure interconnection of the wire guides 10, 20, and are sized to provide easy connection between coupling wire guide 20 and various sized wire guides 10. At the same time, the loops 34, 36, 38 are sufficiently flexible to provide a low profile for the coupling wire guide 20, and additionally may be easily removed or shifted in position depending on the needs of the user. Further, the atraumatic nature of the distal tip 32 is maintained, as is the preferred balance between flexibility and rigidity of the main body 22. In this manner, the coupling wire guide 20 is increasingly adept at traversing the vasculature, and in particular torturous pathways, while at the same time having sufficient rigidity for straightening out these passageways and passing through occlusions or other obstacles.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for coupling to a previously introduced wire guide during intracorporeal procedures, the coupling wire guide comprising:

a main body defined by at least a first wire, the main body extending along a longitudinal axis, the first wire wound around a safety wire to define a plurality of revolutions have a predetermined size and pitch;

a first loop defined by an enlarged revolution of the first wire within a distal portion of the main body, the first loop sized to receive the previously introduced wire guide therein; and the first wire, at a position distal to the first loop and enlarged revolution, again forms a plurality of revolutions having the predetermined size, the first wire maintaining the pitch from a position proximal to the first loop to the portion distal to the first loop.

2. The coupling wire guide of claim 1, further comprising a second wire wound around the safety wire, the first and second wires defining the main body, and further comprising a second loop defined by an enlarged revolution of one of the first or second wires within the distal portion within a distal portion of the main body.

3. The coupling wire guide of claim 2, wherein the first and second loops are longitudinally spaced apart.

4. The coupling wire guide of claim 2, wherein the first and second loops are formed by the first and second wires, respectively.

5. The coupling wire guide of claim 2, wherein the first and second wires do not change pitch in the area of the first and second loops relative to the predetermined pitch at the position proximal to the first loop.

6. The coupling wire guide of claim 2, wherein the first and second wires abut each other on their lateral sides as they form the plurality of revolutions of predetermined size.

7. The coupling wire guide of claim 2, wherein the position distal to the first loop, where the first wire again forms a plurality of revolutions having the predetermined size, is located proximal to the second loop.

8. The coupling wire guide of claim 1, further comprising a third wire wound around the safety wire, the first, second and third wires defining the main body.

9. The coupling wire guide of claim 8, further comprising a third loop defined by an enlarged revolution of one of the first, second or third wires within the distal portion of the main body.

10. The coupling wire guide of claim 9, wherein the first, second and third loops are axially spaced apart a distance about equal to the pitch of the coiled first, second and third wires.

11. The coupling wire guide of claim 1, wherein the main body does not curve back on itself to form the first loop.

12. The coupling wire guide of claim 1, wherein the first loop is flexible and can fold radially inwardly.

13. A coupling wire guide for coupling to a previously introduced wire guide during intracorporeal procedures, the coupling wire guide comprising:

a main body defined by a first wire, a second wire and a third wire, the main body extending along a longitudinal axis, the first, second and third wires coiled in parallel around the longitudinal axis;

the first wire defining a first loop at a distal portion of the main body;

the second wire defining a second loop at the distal portion of the main body; and the third wire defining a third loop at the distal portion of the main body wherein the first, second and third loops do not overlap in the longitudinal direction, wherein the first, second and third wires are coiled at a predetermined pitch that is maintained from a location proximal to the first loop to a location distal to the third loop.

14. The coupling wire guide of claim 13, wherein the first, second and third loops are sized to receive the previously introduced wire guide.

15. The coupling wire guide of claim 13, wherein the second loop is positioned distally from the first loop.

16. The coupling wire guide of claim 13, wherein an area of the first loop is sized to receive a previously introduced wire guide having a 0.014 inch diameter.

17. The coupling wire guide of claim 13, wherein the first and second wires, at positions distal to the first and second loops respectively, again form a plurality of revolutions having the predetermined size at positions located proximal to the second and third loops, respectively.

* * * * *